United States Patent
Schenider et al.

(10) Patent No.: US 9,539,446 B2
(45) Date of Patent: *Jan. 10, 2017

(54) LOW CHLORINE ODOR CONTROL COMPOSITIONS

(76) Inventors: David J. Schenider, Union, KY (US); Charles A. Schneider, Villa Hills, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/105,954

(22) Filed: May 12, 2011

(65) Prior Publication Data

US 2012/0003173 A1 Jan. 5, 2012

Related U.S. Application Data

(60) Provisional application No. 61/334,678, filed on May 14, 2010.

(51) Int. Cl.
*A61Q 19/00* (2006.01)
*A61L 15/46* (2006.01)
(Continued)

(52) U.S. Cl.
CPC .............. *A61Q 19/00* (2013.01); *A61K 8/466* (2013.01); *A61L 15/46* (2013.01); *A61K 2800/10* (2013.01);
(Continued)

(58) Field of Classification Search
CPC ..... C07C 311/15; A61Q 19/00; A61Q 17/005; A61F 5/44; A61F 5/4401; A61F 13/20; A61F 13/00068; A61F 13/0206; A61F 13/49
See application file for complete search history.

(56) References Cited

U.S. PATENT DOCUMENTS 3,634,261 A 1/1972 Keay et al.
5,201,326 A * 4/1993 Kubicki et al. ............... 128/832
(Continued)

FOREIGN PATENT DOCUMENTS

WO WO 2010/099110 A2 9/2010

OTHER PUBLICATIONS

Nakamura A. "Stress Repression in Restrained Rats by R-(-)-Linalool Inhalation and Gene Expression Profiling of Their Whole Blood Cells"; J. Agric. Food Chem. (2009), 57, p. 5480-5485.*
(Continued)

*Primary Examiner* — Aradhana Sasan
(74) *Attorney, Agent, or Firm* — Richard M. Klein; Fay Sharpe LLP

(57) ABSTRACT

An odor control composition includes (a) at least one fragrance and (b) a halo active aromatic sulfonamide compound of Formula (I):

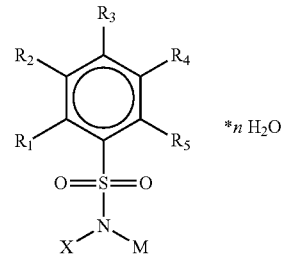

Formula (I)

wherein $R_1$, $R_2$, $R_3$, $R_4$, and $R_5$ are independently selected from hydrogen, COOR', CON(R")$_2$, alkoxy, CN, NO$_2$, SO$_3$R", halogen, substituted or unsubstituted phenyl,
(Continued)

sulfonamide, halosulfonamide, and substituted or unsubstituted $C_1$-$C_{12}$ alkyl;

R' is hydrogen, an alkali metal, an alkaline earth metal, substituted $C_1$-$C_{12}$ alkyl, or unsubstituted $C_1$-$C_{12}$ alkyl; and R" is hydrogen or substituted or unsubstituted $C_1$-$C_{12}$ alkyl, where the two R" groups in $CON(R")_2$ may be independently selected;

X is halogen;

M is an alkali or alkaline earth metal; and n is the number of water molecules per molecule of the sulfonamide compound.

5 Claims, 3 Drawing Sheets

(51) Int. Cl.
| | | |
|---|---|---|
| *A61K 8/46* | (2006.01) | |
| *A61Q 5/02* | (2006.01) | |
| *A61Q 17/04* | (2006.01) | |
| *A61Q 5/06* | (2006.01) | |

(52) U.S. Cl.
CPC . *A61Q 5/02* (2013.01); *A61Q 5/06* (2013.01); *A61Q 17/04* (2013.01)

(56) References Cited

U.S. PATENT DOCUMENTS

| | | | |
|---|---|---|---|
| 7,371,368 B2 | 5/2008 | Schneider et al. | |
| 7,384,899 B2* | 6/2008 | Schneider et al. | 510/160 |
| 7,465,829 B2* | 12/2008 | Schneider et al. | 564/84 |
| 7,560,592 B2 | 7/2009 | Schneider et al. | |
| 2003/0100871 A1 | 5/2003 | Mauro et al. | |
| 2004/0062742 A1 | 4/2004 | Winston et al. | |
| 2005/0287109 A1* | 12/2005 | Schneider et al. | 424/78.1 |
| 2006/0280766 A1* | 12/2006 | Schneider et al. | 424/405 |
| 2008/0286224 A1* | 11/2008 | Vega et al. | 424/78.31 |
| 2008/0299054 A1* | 12/2008 | Chandar et al. | 424/54 |
| 2009/0087401 A1* | 4/2009 | Hiramoto et al. | 424/76.1 |
| 2010/0278767 A1* | 11/2010 | Hoffkes et al. | 424/62 |

OTHER PUBLICATIONS

Vesna, "Bicarb soda: natural body deoderant" p. 1; Mar. 11, 2009; (http://sustainableecho.com/bicarb-soda-natural-body-deodorant/).*

Chery Lin Skin Therapy "Chemical consitituents of essential oils", pp. 1-4; May 2007.*

"Aroma compounds", Wikipedia, Mar. 30, 2010 , pp. 1-7.*

Vuorela et al., "Extraction of the Volatile Oil in Chamomile Flowerheads Using Supercritical Carbon Dioxide," Flavour and Fragrance Journal, vol. 5, 81-84 (1990).*

International Search Report Aug. 12, 2011.

International Search Report of International Application No. PCT/US11/36170 dated Aug. 12, 2011.

Gottardi, Aqueous Chloramine T Solutions as Skin Disinfectants: Chemical Compostion, Reactivity, and Toxicity; Arch. Pharm. (Weinheim); http://onlinelibrary.wiley.com; pp. 377-384; Dec. 18, 1990.

Extended European Search Report for European Application No. 11781251.1 dated Sep. 23, 2014.

* cited by examiner

LOW CHLORINE ODOR CONTROL COMPOSITIONS

CROSS-REFERENCE TO RELATED APPLICATIONS

This application claims priority to U.S. Provisional Patent Application Ser. No. 61/334,678, filed May 14, 2010. The disclosure of that application is hereby fully incorporated by reference herein.

BACKGROUND

The present disclosure relates to odor control compositions having little or no chlorine associated smell. Also disclosed are absorbent members comprising the compositions, personal care products comprising the compositions, and processes for making and using the same.

Odor control compositions neutralize and/or destroy targeted odor-causing molecules. The odor-causing molecules may be present in bodily fluids such as blood, pus, sweat, semen, secretions, menstrual discharge, urine, and fecal matter. While the undesirable smell of the odor-causing molecules can be reduced or eliminated, the odor control composition itself may have a strong, pungent chlorine-like smell which is irritating, unacceptable, or unwanted in certain applications.

It would be desirable to develop an odor control composition that exhibits a reduced chlorine smell, or no chlorine smell at all.

BRIEF DESCRIPTION

Disclosed herein, in various embodiments, are odor control compositions having little or no chlorine associated smell.

Disclosed in embodiments is an odor-controlling composition having reduced chlorine smell, comprising: at least one fragrance; and a halo active aromatic sulfonamide compound of Formula (I):

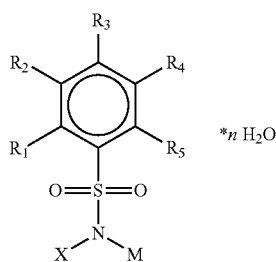

Formula (I)

wherein $R_1$, $R_2$, $R_3$, $R_4$, and $R_5$ are independently selected from hydrogen, COOR', CON(R")$_2$, alkoxy, CN, NO$_2$, SO$_3$R", halogen, substituted or unsubstituted phenyl, sulfonamide, halosulfonamide, and substituted or unsubstituted $C_1$-$C_{12}$ alkyl;
R' is hydrogen, an alkali metal, an alkaline earth metal, substituted $C_1$-$C_{12}$ alkyl, or unsubstituted $C_1$-$C_{12}$ alkyl; and
R" is hydrogen or substituted or unsubstituted $C_1$-$C_{12}$ alkyl, where the two R" groups in CON(R")$_2$ may be independently selected;
X is halogen;
M is an alkali or alkaline earth metal; and
n is the number of water molecules per molecule of the sulfonamide compound.

In particular embodiments, at least two of $R_1$, $R_2$, $R_3$, $R_4$, and $R_5$ are not hydrogen. In other embodiments, $R_3$ is COOR'. In particular, R' is an alkali or alkaline earth metal.

In other embodiments, $R_3$ is COOR'; $R_2$ and $R_4$ are identical to each other; and $R_1$ and $R_5$ are hydrogen. In alternative embodiments, $R_3$ is COOR'; $R_2$ and $R_4$ are hydrogen; and $R_1$ and $R_5$ are identical to each other. In still other embodiments, $R_3$ is COOR', and at least one of $R_1$, $R_2$, $R_4$, and $R_5$ is not hydrogen.

In particular combinations, the composition has two sulfonamide compounds of Formula (I), where the sulfonamide compounds are of Formulas (III) and (IV):

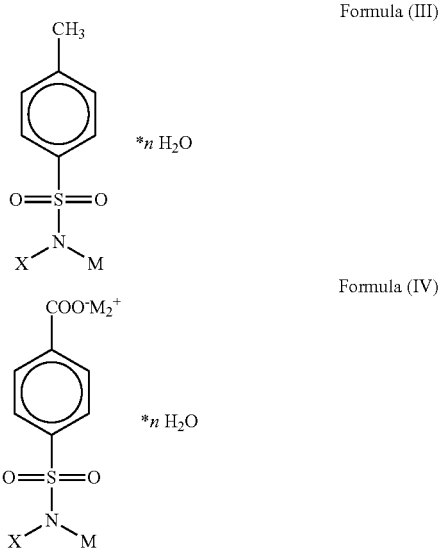

Formula (III)

Formula (IV)

wherein $M_2$ is hydrogen, an alkali metal, or an alkali earth metal; X is halogen, M is independently an alkali or alkaline earth metal; and n is the number of water molecules per molecule of each sulfonamide compound.

The weight ratio of Formula (III) to Formula (IV) can be from about 1:2 to about 1:4.

Also disclosed is an absorbent member comprising: an absorbent material; and an odor controlling composition comprising at least one fragrance and a halo active aromatic sulfonamide compound of Formula (I):

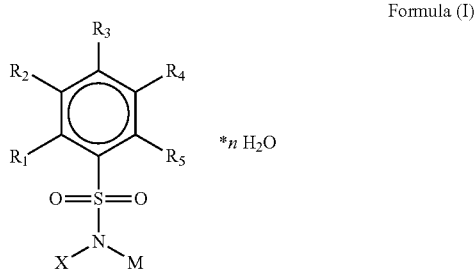

Formula (I)

wherein $R_1$, $R_2$, $R_3$, $R_4$, and $R_5$ are independently selected from hydrogen, COOR', CON(R")$_2$, alkoxy, CN, NO$_2$, SO$_3$R", halogen, substituted or unsubstituted phenyl, sulfonamide, halosulfonamide, and substituted or unsubstituted $C_1$-$C_{12}$ alkyl;

R' is hydrogen, an alkali metal, an alkaline earth metal, substituted $C_1$-$C_{12}$ alkyl, or unsubstituted $C_1$-$C_{12}$ alkyl; and R" is hydrogen or substituted or unsubstituted $C_1$-$C_{12}$ alkyl, where the two R" groups in CON(R")$_2$ may be independently selected;

X is halogen;

M is an alkali or alkaline earth metal; and n is the number of water molecules per molecule of the sulfonamide compound.

The absorbent material can be a polymer, cellulosic fiber, or a wood fluff. The absorbent member could be in the form of a flat sheet. The absorbent member may be used in a diaper, a sanitary napkin, a tampon, a wound dressing, or a bandage.

Also disclosed is a process for making an odor-controlling bodily fluid absorbent member, comprising: providing an absorbent material; treating the absorbent material with a solution; and shaping the absorbent material to form the absorbent member; wherein the solution comprises at least one fragrance and a halo active aromatic sulfonamide compound of Formula (I):

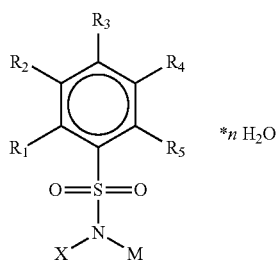

Formula (I)

wherein $R_1$, $R_2$, $R_3$, $R_4$, and $R_5$ are independently selected from hydrogen, COOR', CON(R")$_2$, alkoxy, CN, NO$_2$, SO$_3$R", halogen, substituted or unsubstituted phenyl, sulfonamide, halosulfonamide, and substituted or unsubstituted $C_1$-$C_{12}$ alkyl;

R' is hydrogen, an alkali metal, an alkaline earth metal, substituted $C_1$-$C_{12}$ alkyl, or unsubstituted $C_1$-$C_{12}$ alkyl; and R" is hydrogen or substituted or unsubstituted $C_1$-$C_{12}$ alkyl, where the two R" groups in CON(R")$_2$ may be independently selected;

X is halogen;

M is an alkali or alkaline earth metal; and n is the number of water molecules per molecule of the sulfonamide compound.

Also disclosed is a personal care product, comprising a base and an odor controlling composition comprising at least one fragrance and a halo active aromatic sulfonamide compound of Formula (I):

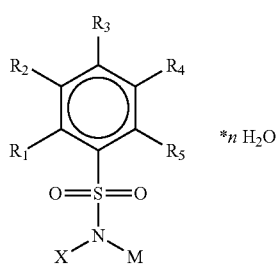

Formula (I)

wherein $R_1$, $R_2$, $R_3$, $R_4$, and $R_5$ are independently selected from hydrogen, COOR', CON(R")$_2$, alkoxy, CN, NO$_2$, SO$_3$R", halogen, substituted or unsubstituted phenyl, sulfonamide, halosulfonamide, and substituted or unsubstituted $C_1$-$C_{12}$ alkyl;

R' is hydrogen, an alkali metal, an alkaline earth metal, substituted $C_1$-$C_{12}$ alkyl, or unsubstituted $C_1$-$C_{12}$ alkyl; and R" is hydrogen or substituted or unsubstituted $C_1$-$C_{12}$ alkyl, where the two R" groups in CON(R")$_2$ may be independently selected;

X is halogen;

M is an alkali or alkaline earth metal; and n is the number of water molecules per molecule of the sulfonamide compound.

These and other non-limiting features or characteristics of the present disclosure will be further described below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
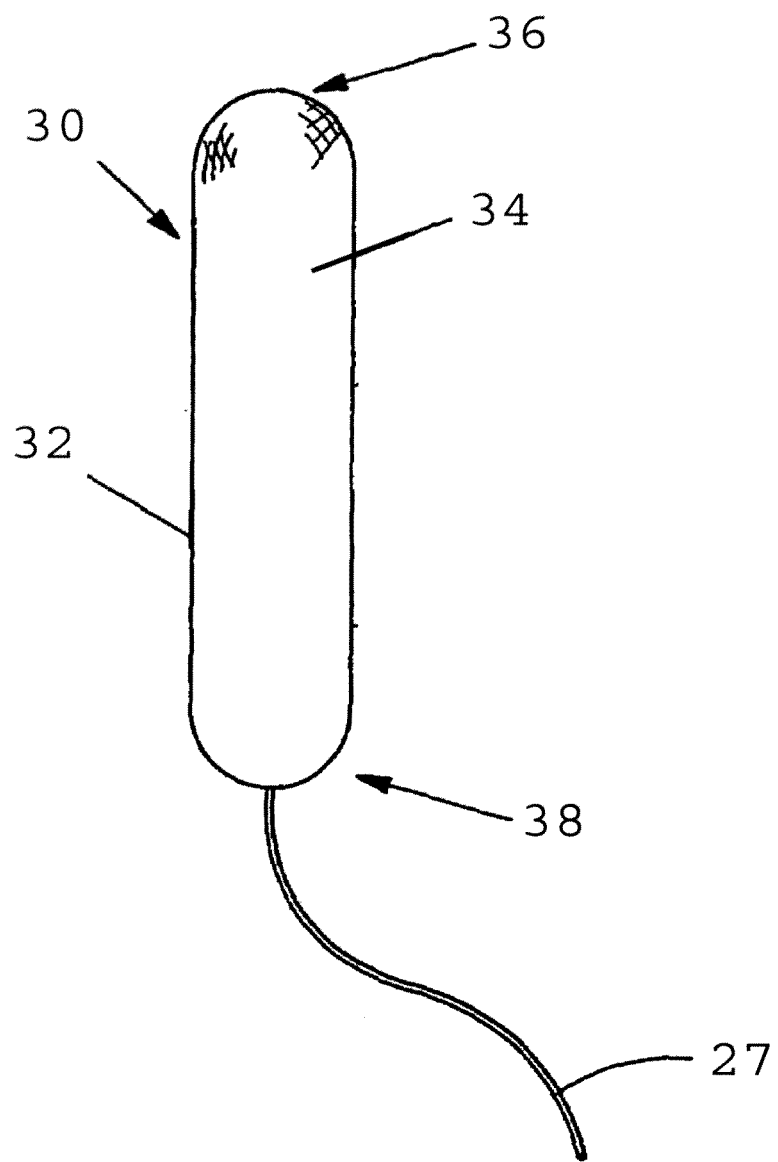
FIG. 1 is a side view of a tampon formed from an absorbent member of the present disclosure.

A more complete understanding of the components, processes, and apparatuses disclosed herein can be obtained by reference to the accompanying drawings. These figures are merely schematic representations based on convenience and the ease of demonstrating the present disclosure, and are, therefore, not intended to indicated relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The modifier "about" used in connection with a quantity is inclusive of the stated value and has the meaning dictated by the context (for example, it includes at least the degree of error associated with the measurement of the particular quantity). In addition, the value or range endpoints so modified should also be considered as being disclosed. For example, the range "about 2 to about 4" should also be considered as disclosing the range "2 to 4".

Halo active aromatic sulfonamide organic compounds are known. Chloramine-T is an example of a sulfonamide organic compound which has been used in many applications. The usefulness of Chloramine-T is predicated on its ability to release an active Cl+ ion when needed on demand, immediately after which, it simultaneously generates an active aromatic sulfo nitrene companion ion. The active Cl+ ion and the companion aromatic sulfo nitrene ion may work together to degrade odor-causing molecules. The term "Cl+" refers to the fact that the chlorine atom has a +1 formal charge in a hypochlorite ion, ClO$^-$, which is the form taken by the chlorine atom when dissociated from the sulfonamide compound. A chlorine atom is generally considered to have a charge of 1⁻. Reference to the chlorine atom as having a +1 or 1⁻ charge may be used in this application interchangeably because this terminology has no effect on the compound itself or its use.

Most odor causing molecules are mercaptans, sulfides heterocyclic or amine based compounds. Halo active aromatic sulfonamide compounds are excellent agents for eliminating odors from these classes of compounds as both the Cl+ cations and the sulfonamide moiety remaining after the Cl+ cations are produced, react with the odor causing molecule(s).

The present disclosure relates to odor control compositions that exhibit little to no chlorine smell. At least two types of such odor control compositions are contemplated here. The first type of odor control composition comprises certain halo active aromatic sulfonamide compounds of Formula (I), as will be discussed further herein. The second type of odor control composition comprises (a) at least one fragrance; and (b) a halo active aromatic sulfonamide compound of Formula (I), as discussed further herein. These odor control compositions can be used in personal care products to control odor without themselves producing a noticeable chlorine smell.

Odor control compositions having reduced chlorine smell may comprise certain halo active aromatic sulfonamide compounds of Formula (I):

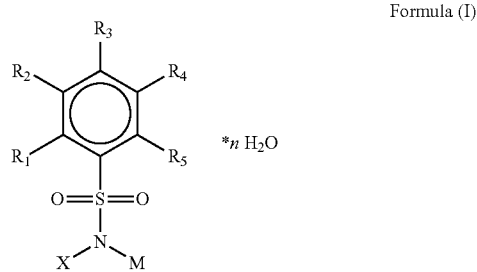

Formula (I)

wherein $R_1$, $R_2$, $R_3$, $R_4$, and $R_5$ are independently selected from hydrogen, COOR', CON(R")$_2$, alkoxy, CN, NO$_2$, SO$_3$R", halogen, substituted or unsubstituted phenyl, sulfonamide, halosulfonamide, and substituted or unsubstituted C$_1$-C$_{12}$ alkyl;
R' is hydrogen, an alkali metal, an alkaline earth metal, substituted C$_1$-C$_{12}$ alkyl, or unsubstituted C$_1$-C$_{12}$ alkyl; and
R" is hydrogen or substituted or unsubstituted C$_1$-C$_{12}$ alkyl, where the two R" groups in CON(R")$_2$ may be independently selected;
X is halogen;
M is an alkali or alkaline earth metal; and
n is the number of water molecules per molecule of the sulfonamide compound.

It should be noted that the term "aromatic", as used herein, refers to the chemical property of conjugated bonds whose delocalized electrons contribute to the stability of the overall compound, and will not be used to refer to smell.

Generally, M is sodium or potassium. X is generally chlorine, bromine, fluorine, or iodine, and in particular embodiments is chlorine. Compounds of Formula (I) may or may not be hydrated, as indicated by the variable n. In particular embodiments, the compounds of Formula (I) are a trihydrate (i.e., n=3). In other embodiments, the compound is in a solid form, such as a powder.

When the phenyl and/or alkyl group is substituted, one or more hydrogen atoms may be independently replaced with hydroxyl or halogen.

When $R_1$, $R_2$, $R_4$, and $R_5$ are hydrogen, and $R_3$ is methyl, the compound of Formula (I) is also known as chloramine-T. When $R_1$, $R_2$, $R_3$, $R_4$, and $R_5$ are hydrogen, the compound of Formula (I) is also known as chloramine-B.

In some embodiments of Formula (I), at least two of $R_1$, $R_2$, $R_3$, $R_4$, and $R_5$ are not hydrogen.

In particular embodiments of Formula (I), $R_3$ is COOR'; R' is hydrogen, an alkali metal, an alkaline earth metal, substituted C$_1$-C$_{12}$ alkyl, or unsubstituted C$_1$-C$_{12}$ alkyl; $R_1$, $R_2$, $R_4$, and $R_5$ are independently selected from hydrogen, COOR', CON(R")$_2$, alkoxy, CN, NO$_2$, SO$_3$R", halogen, substituted or unsubstituted phenyl, sulfonamide, halosulfonamide, and substituted or unsubstituted C$_1$-C$_{12}$ alkyl; X is halogen; M is an alkali or alkaline earth metal; and n is the number of water molecules per molecule of the sulfonamide compound. These embodiments contain a 4-carboxy sidechain which has been found to have a highly reduced chlorine smell, particularly compared to chloramine-T. In more specific embodiments, $R_3$ is COOR', and at least one of $R_1$, $R_2$, $R_4$, and $R_5$ is not hydrogen. In other more specific embodiments, the R' of $R_3$ is an alkali or alkaline earth metal.

In yet other embodiments of Formula (I), $R_3$ is COOR'; $R_2$ and $R_4$ are identical to each other; and $R_1$ and $R_5$ are hydrogen.

In yet other embodiments of Formula (I), $R_3$ is COOR'; $R_2$ and $R_4$ are hydrogen; and $R_1$ and $R_5$ are identical to each other.

In other embodiments of Formula (I), the halo active aromatic sulfonamide compound is an N-chloro-p-carboxysulfonamide represented by the structure of Formula (II):

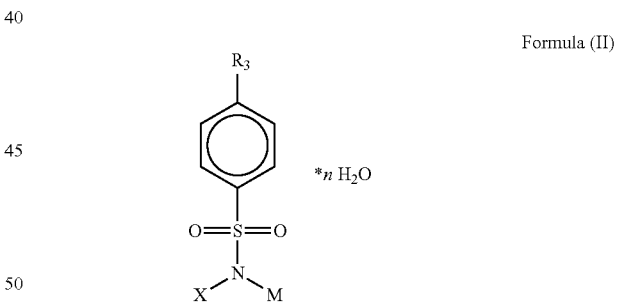

Formula (II)

wherein $R_3$ is COOR'; R' is hydrogen, an alkali metal, an alkaline earth metal, substituted C$_1$-C$_{12}$ alkyl, or unsubstituted C$_1$-C$_{12}$ alkyl; X is halogen; M is an alkali or alkaline earth metal; and n is the number of water molecules per molecule of the sulfonamide compound. The p-carboxysulfonamide compound of Formula (II) is also referred to herein as BENZ. BENZ exhibits a lower chlorine smell than chloramine-T or chloramine-B. When BENZ is combined with at least one fragrance, there is no detectable chlorine smell for most humans.

In some embodiments, two different sulfonamide compounds are used in the odor control composition. In particular, the sulfonamide compounds differ in properties such as odor-controlling ability, stability, and cost. It may be desirable to use a mixture of two or more compounds to balance odor-controlling properties with economic factors such as cost and availability of the sulfonamide compounds. For example, each sulfonamide compound may have a different reaction rate, stability, and/or release rate, or neutralize different odor-causing molecules more efficiently. The weight ratio between the two sulfonamide compounds may range from about 90:10 to about 10:90, or from about 70:30 to about 30:70.

In specific embodiments, the two sulfonamide compounds are N-chloro-p-toluenesulfonamide (i.e. chloramine-T) and N-chloro-p-carboxysulfonamide. These two compounds are shown below as Formulas (III) and (IV):

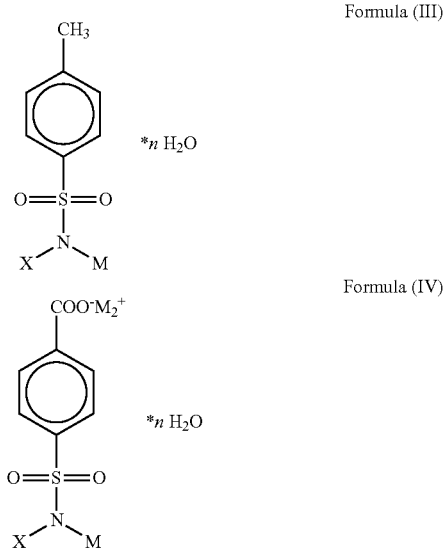

wherein $M_2$ is hydrogen, an alkali metal, or an alkali earth metal; X is halogen, M is independently an alkali or alkaline earth metal; and n is the number of water molecules per molecule of each sulfonamide compound. Desirably, $M_2$ is hydrogen, sodium, or potassium. In some particular embodiments, the weight ratio of Formula (III) to Formula (IV) is from about 1:2 to about 1:4.

The halo active aromatic sulfonamide compounds of Formula (I) are stable and do not decompose in aqueous solution, allowing the absorbent member to have a long shelf life.

The odor control composition may also comprise a fragrance. The term "fragrance", as used herein, refers to one or more chemical compounds that, when combined with the halo active aromatic sulfonamide compound of Formula (I), produces an odor control composition that does not exhibit a chlorine-like smell.

Many different fragrances are known in the art. However, only certain fragrances result in a composition that does not exhibit a chlorine-like smell. In particular, it has been found that certain combinations of sulfonamide with fragrance which were expected to result in a composition without chlorine-like smell, did not perform as expected. The choice of the fragrance is critical and is not obvious.

Suitable fragrances are commercially available from manufacturers such as Givaudan and Horizon Aromatics. The following table of fragrances lists the name of some exemplary fragrances:

TABLE 1

| Fragrance Name |
| --- |
| Fabric Delight 1 |
| Lavender & Chamomile |
| Linen Basket |
| Outdoor Clean |
| Rain Garden GNF |
| Fragrance Duplicate A |
| Fragrance Duplicate B |

In this regard, it is known that the active compounds in lavender are linalool and linalyl acetate, and an active compound in chamomile is bisabolol. Thus, the fragrance may be selected from linalool, linalyl acetate, or bisabolol.

Other "tracer" odorants may also be present in the odor control composition that help the user know where s/he has applied the odor control composition. Such tracer odorants leave the composition rapidly upon application, generally in under a minute.

The odor control composition may comprise from about 0.01 to about 10 wt % of the halo active aromatic sulfonamide compound. In some embodiments, the composition may comprise from about 0.1 to about 5 wt % of the halo active aromatic sulfonamide compound. In other embodiments, the composition may comprise from about 0.25 to about 1.5 wt %, or from about 0.5 to about 1.0 wt %, of the halo active aromatic sulfonamide compound.

The fragrance may be present in an amount of from about 0.005 to about 5 wt % of the odor control composition. In some embodiments, the fragrance may be present in an amount of from about 0.01 to about 1 wt % of the odor control composition. In other embodiments, the fragrance may be present in an amount of from about 0.025 to about 0.5 wt %, or from about 0.05 to about 0.1 wt %, of the odor control composition.

For stability and for optimum performance, the pH of the composition should be between 6 and 14, though generally the pH should be kept between 8 and 9.5, or from 8.5 to 9. As urine can have a pH ranging from 4.5 to 8, and is generally acidic, this pH range also helps to neutralize urine. It appears that the p-carboxy derivative is stable down to a pH of about 6.5, while chloramine-T is most stable at pH's greater than 7.5.

In order to maintain the solution within these pH ranges, a buffering agent may be added to the odor control composition. The buffering agent can compensate for any change in pH that may result from the acidity of the urine, the conditions of application, and/or the nature of the odor causing molecule. Exemplary buffering agents include sodium bicarbonate, potassium bicarbonate, sodium carbonate, potassium carbonate, acetate buffers (such as sodium acetate), phosphate buffers (such as tri and di sodium phosphate and mixtures thereof, pH blended phosphates, sulfate buffers (such as di and tri sodium sulfate), and mixtures thereof. The buffering agent can be added up to the limit of solubility. Preferred buffering agents are potassium and sodium biocarbonate.

The use of these bicarbonates in the disclosed compositions also appears to decrease color which may be due to pH effects. In particular, bicarbonates reduce the yellow color of BENZ solutions drastically. This effect may be highly desirable in some applications such as laundry and diaper applications.

The buffering agent may be present in an amount of from 0 to about 5 wt % of the odor control composition. In some embodiments, the composition comprises from about 0.25 to about 1 wt % buffering agent. In other embodiments, the composition comprises from about 0.25 to about 0.5 wt % buffering agent.

A low molecular weight alcohol may also be added to the odor control composition to enhance the activity of the sulfonamide compound. An exemplary alcohol is t-butanol. The alcohol may have several effects. The alcohol enhances the odor removal activity of the active aromatic N-halo sulfonamide group. The alcohol can also increase surface activity or enable the use of a more favorable blend of fragrances. The type of alcohol used, however, is somewhat limited. T-butanol or related tertiary alcohols are preferred because they do not contain hydrogen atoms alpha to the oxygen alcohol moiety, and allow for greater stability. The alpha hydrogen atoms apparently detract from stability due to interaction with the active halogen contained in the active aromatic halo sulfonamide compound. However, at pH>10, alcohols containing alpha hydrogen atoms, such as ethanol and isopropanol, were found to not affect stability.

The alcohol may be present in an amount of from 0 to about 5 wt % of the odor control composition. In some embodiments, the odor control composition comprises from about 0.1 to about 3 wt % of the alcohol. In other embodiments, the odor control composition comprises from about 0.25 to about 1 wt %, or from about 0.25 to about 0.5 wt %, of the alcohol.

A surfactant, or wetting agent, can also be added to the odor control composition. The surfactant decreases surface tension, allowing the sulfonamide compound to be more easily activated when contacted by the bodily fluid. Both non-ionic and anionic surfactants can be used. However, in specific embodiments, a surfactant is not used.

The sulfonamide compound, fragrance, and optional ingredients (tracer odorant, buffering agent, low molecular weight alcohol, and wetting agent) are generally applied as a mixture. For example, the sulfonamide compound and fragrance may be mixed with water or another liquid to form an aqueous or other solution which is useful as the odor control composition. The solution is usually made of one or more sulfonamide compounds, up to the saturation point in solution of the compound(s). This may range from 5% to 25% by weight in aqueous solution, depending on the solubility of the compound and the solvent (alcohol or other).

The odor control compositions of the present disclosure are useful in many different productions and many different environments. For example, they can be used on fabrics or hard surfaces in industrial, commercial, and institutional environments such as hospitals. They can also be used in personal care products, particularly those that contact the skin, because the odor control compositions do not have a chlorine smell and do no irritate the skin. Exemplary personal care products can include air fresheners, candles; fabric fresheners, laundry detergents, dishwashing liquids; surface cleaners, glass cleaners; chapstick, lip gloss, lipstick; cologne, perfume; cotton swabs; deodorants; eyeliner, makeup; tissues; lotion, skin cream, sunscreen, moisturizer, talcum powder, shaving cream; lubricants; shampoo, hairspray, bath/body wash; polishes (wood, wax, etc.); bandages, gauze pads; disposable gloves; soap, wipes, tape; and diapers, sanitary napkins, or tampons. Such personal care products generally have a base, which can be a solid, gel, or liquid. The odor control composition is dispersed within or upon the base.

The odor control compositions may be used in odor-controlling bodily fluid absorbent members. The odor-controlling bodily fluid absorbent members of the present disclosure generally comprise (i) an absorbent material or substrate; and (ii) an odor control composition as described above. The absorbent material or substrate is treated with the odor control composition, or in other words, the odor control composition is generally dispersed within or throughout the absorbent material. The absorbent material is then shaped to form the absorbent member. The absorbent member may be used in, for example, a diaper or other sanitary product.

The odor control composition can be added to the absorbent material using known methods. In particular, when the absorbent material is wood fluff, the odor control composition can be added prior to fluffing when the wood is still in the form of a sheet of wood fibers, or the sulfonamide compound can be added after fluffing has occurred and the wood is in the form of a fibrous, cotton-like material. The active ingredients can be impregnated into or dispersed throughout the absorbent material.

For example, the odor control solution is sprayed on the absorbent material. The solvent is then allowed to evaporate, leaving behind the active sulfonamide compound and fragrance. Multiple sprays can be used to increase the amount of active sulfonamide compound on the absorbent material.

The odor-controlling bodily fluid absorbent members of the present disclosure are useful for controlling odor in sanitary products such as diapers, sanitary napkins, etc, or as wipes for general use (i.e. as a thin flat sheet). The absorbent members are also useful in products such as wound dressings, bandages, etc. Generally, the absorbent member is contacted with the bodily fluid, and the sulfonamide compound neutralizes odor-causing molecules in the bodily fluid. For example, the absorbent member may be located in a diaper, and urine or feces subsequently contact the absorbent member. Alternatively, the absorbent member is part of a bandage which is applied to a wound that oozes pus, and the absorbent member contacts the pus.

The shape of the odor-controlling bodily fluid absorbent member can be varied depending on its use; for example, it can be made as a flat sheet or in a tubular form. It should be noted that the absorbent member is generally only one part of the overall consumer article.

For example, the absorbent member may be used to form a tampon. Referring to FIG. 1, the tampon 30 comprises an absorbent member 32 which has been compressed or shaped into a tube. Prior to compression, the absorbent member may have any suitable size and thickness suitable for compression into a tampon having a vaginally insertable shape. The absorbent member is generally square or rectangular prior to compression. A typical size for the absorbent member prior to compression may be from about 40 mm to about 100 mm in length and from about 40 mm to about 80 mm in width. The absorbent member 22 has an exterior surface 34, and an insertion end 36 opposed to a withdrawal end 38. A withdrawal means, such as string 27, extends from the withdrawal end 38. The withdrawal means can take on other forms such as a ribbon, loop, tab, or the like, and may be attached in any suitable manner known in the art including sewing, adhesive attachment, or a combination of known bonding methods. The withdrawal means may be joined to any suitable location on the tampon.

Figure 2:
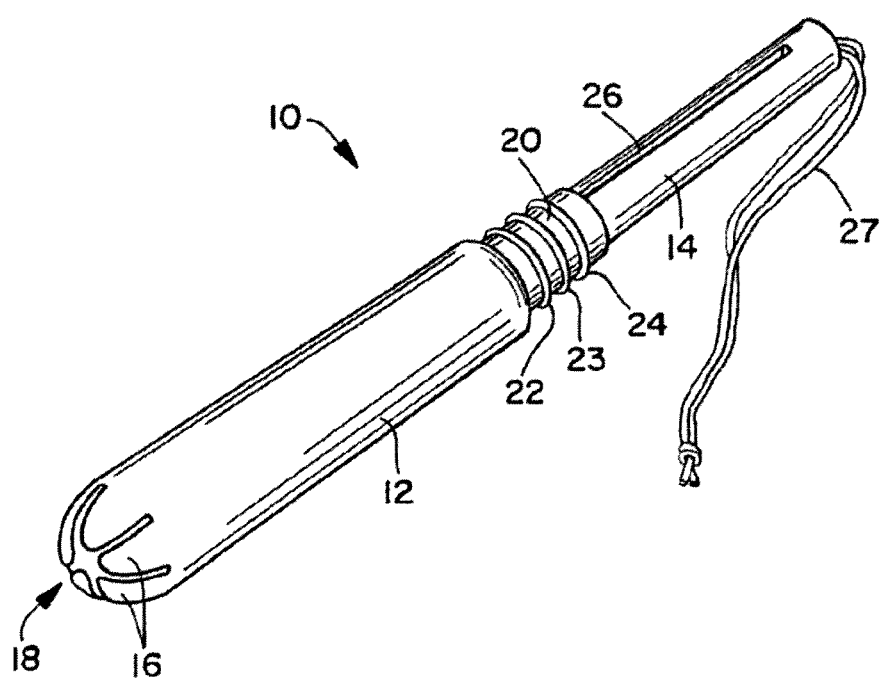
FIG. 2 is a perspective view of a tampon applicator.

The tampon may be inserted digitally or through the use of an applicator. Such applicators typically have a "tube and plunger" type arrangement and may be plastic, paper, or other suitable material. Additionally, a "compact" type applicator is also suitable. Referring to FIG. 2, a compact tampon applicator 10 is shown having an outer tube 12 and an inner tube 14. The outer tube 12 has a series of petals 16 formed at a forward end 18 which is designed to be inserted into a woman's vagina. The outer tube 12 is provided with a gripping portion 20 that includes ridges 22, 23 and 24. The inner tube 14 has an elongated slot 26 that aids in retaining the inner tube 14 in the outer tube 12. The cut-out slot 26 also aids in moving the inner tube 14 relative to the outer tube 12 during use. A withdrawal string 27 is attached to one end of a hollow tampon 28 and extends through the inner tube 14. The withdrawal string 27 is used to withdraw the tampon 28 from the vagina after use. Here, the final article is a tampon with applicator.

Figure 3:
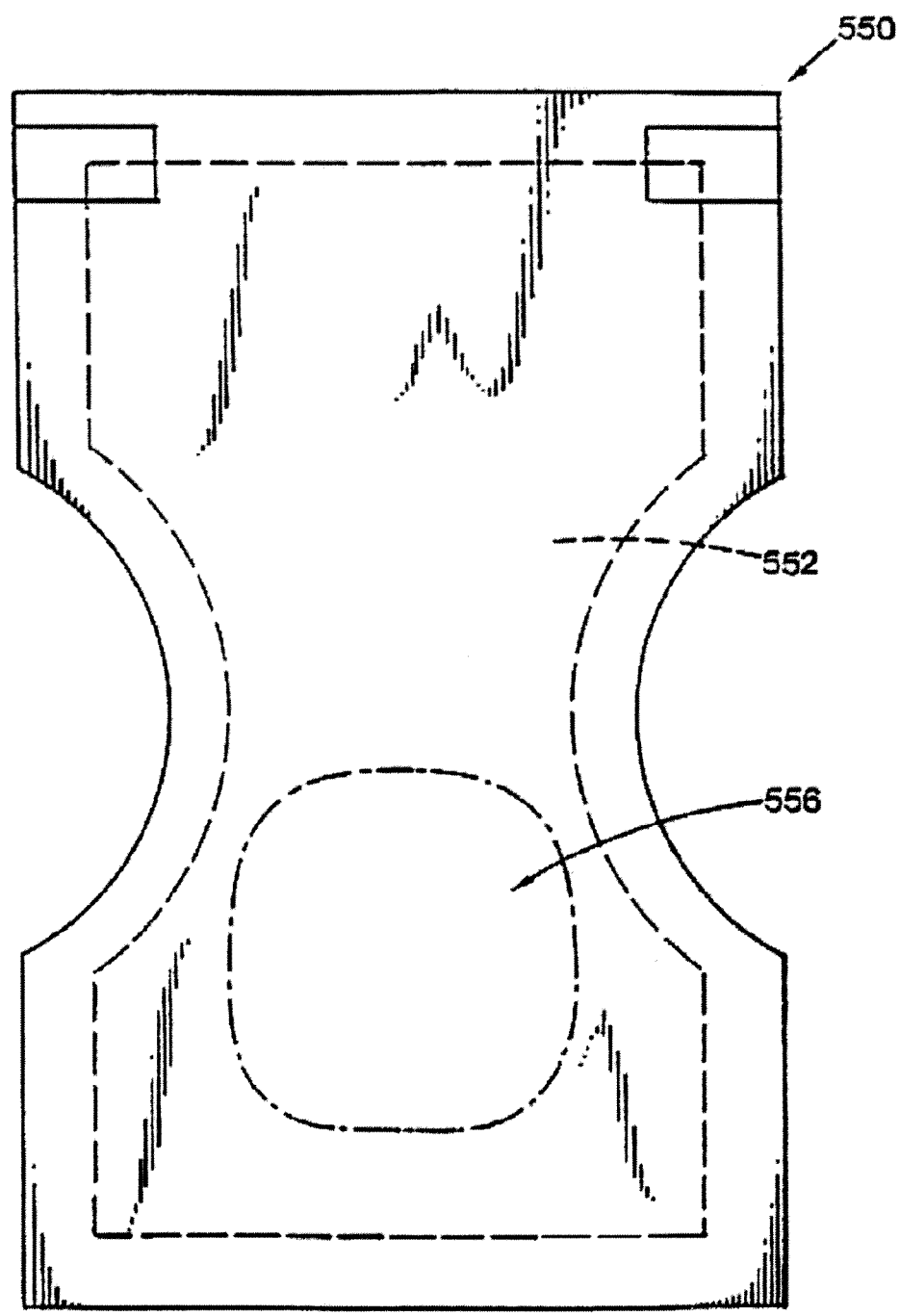
FIG. 3 is a top view of a diaper containing an absorbent member of the present disclosure.

As another example, FIG. 3 illustrates a conventional disposable diaper 550. The diaper includes a liner 554. The absorbent member may be in the shape of a flat sheet, and either be attached to a top side of the liner or inserted into the liner. The absorbent member may be shaped to cover the majority of the liner, as indicated at 552. Alternatively, the absorbent member may be shaped to fit a target zone, for example, the crotch portion of a diaper indicated at 556. Here, the final article is a diaper. Generally speaking, the absorbent member may be engaged with a housing to form a final article.

The absorbent material or substrate may be natural or synthetic. The absorbent material may also be in the form of fibers, powders, or granules, or in larger amounts in the form of sheets, mats, pads, or tubes. Exemplary absorbent materials may include synthetic fibers made from polyacrylates, polyacrylamide copolymers, ethylene maleic anhydride copolymers, polyvinyl alcohol copolymers, cross-linked polyethylene oxide, starch grafted copolymers of polyacrylonitrile, and cellulosic fibers such as cotton, rayon, and wood pulp. In specific embodiments, the absorbent material is a "fluff" made by pulverizing sheets of wood pulp fibers. Additionally, the absorbent materials may be pretreated with surfactants, wetting agents to enhance their wettability, or with antimicrobial agents, pigments, etc.

The efficacy of the odor control composition can be tested in many different ways. In a skin test, the composition is directly applied to the skin of a test subject, usually by spraying on the hand or forearm. The composition is then smelled at various time increments to determine whether it has a chlorine-like smell. In another test, fox urine, which is known to have a very unpleasant odor, is sprayed on a hard or soft surface. The odor control composition is then applied onto the fox urine, and smelled at various time increments to determine both how well it neutralizes the odor of the fox urine as well as whether any chlorine-like smell remains. Blind evaluations can be conducted by the simple expedient of not identifying what is being smelled by the person whose nose is being used to evaluate the compositions.

Desirably, the odor control composition, or the combination of sulfonamide compound with fragrance, has a reduced chlorine-like smell when applied on both skin and on soft surfaces such as curtains, bedsheets, carpets, etc.

In particular embodiments, the odor control composition comprises 0.25 to 1 wt % of the sulfonamide compound(s), 0.25-0.5 wt % bicarbonate, 0.25-0.50 wt % t-butanol, and 0.05-0.10 wt % of the fragrance, with the remainder being water.

In other particular embodiments, the odor control composition comprises about 0.02 wt % of the Lavender & Chamomile fragrance, about 0.02 wt % of the Linen Basket fragrance, about 0.02 wt % of the Rain Garden GNF fragrance, and about 0.9 wt % of the BENZ sulfonamide compound, with the remainder being water.

In other particular embodiments, the odor control composition comprises about 0.02 wt % of the Linen Basket fragrance, about 0.02 wt % of the Outdoor Clean fragrance, about 0.02 wt % of the Fragrance Duplicate B fragrance, about 0.6 wt % of the BENZ sulfonamide compound, and about 0.3 wt % of chloramine-T, with the remainder being water.

The compositions of the present disclosure are illustrated by the following non-limiting examples, it being understood that these examples are intended to be illustrative only and that the present application is not intended to be limited to the materials, conditions, process parameters and the like recited herein. All proportions are by weight unless otherwise indicated.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. An absorbent member comprising:
 an absorbent material; and
 an odor controlling composition comprising
 a fragrance containing linalool, linalyl acetate, and bisabolol;
 a tracer odorant; and
 a sulfonamide compound of Formula (II):

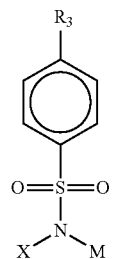

Formula (II)

wherein $R_3$ is COOR'; R' is hydrogen, an alkali metal, an alkaline earth metal, substituted $C_1$-$C_{12}$ alkyl, or unsubstituted $C_1$-$C_{12}$ alkyl; X is halogen; M is an alkali or alkaline earth metal; and n is the number of water molecules per molecule of the sulfonamide compound;
wherein the amount of fragrance is from about 0.05% to about 0.1% by weight of the odor controlling composition.

2. The absorbent member of claim 1, wherein the absorbent material is a polymer, cellulosic fiber, or a wood fluff.

3. The absorbent member of claim 1, wherein the absorbent member is in the form of a flat sheet.

4. The absorbent member of claim 1, wherein the absorbent member is used in a diaper, a sanitary napkin, or a tampon.

5. A personal care product, comprising:
 a base; and
 an odor controlling composition comprising:
 a fragrance containing linalool, linalyl acetate, and bisabolol;
 a tracer odorant; and a sulfonamide compound of Formula (II):

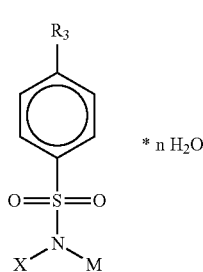

Formula (II)

wherein $R_3$ is COOR'; R' is hydrogen, an alkali metal, an alkaline earth metal, substituted $C_1$-$C_{12}$ alkyl, or unsubstituted $C_1$-$C_{12}$ alkyl; X is halogen; M is an alkali or alkaline earth metal; and n is the number of water molecules per molecule of the sulfonamide compound;
  wherein the personal care product is a diaper, a sanitary napkin, or a tampon;
  wherein the amount of fragrance is from about 0.05% to about 0.1% by weight of the odor controlling composition.

* * * * *